(12) United States Patent
Pereira et al.

(10) Patent No.: US 6,399,799 B1
(45) Date of Patent: Jun. 4, 2002

(54) MONOALKYL QUATS

(75) Inventors: Abel G. Pereira, Belleville; Kostas Nikolopoulos, Piscataway, both of NJ (US)

(73) Assignee: Croda, Inc., Parsippany, NJ (US)

( * ) Notice: Subject to any disclaimer, the term of this patent is extended or adjusted under 35 U.S.C. 154(b) by 0 days.

(21) Appl. No.: 09/409,204

(22) Filed: Sep. 30, 1999

Related U.S. Application Data

(60) Provisional application No. 60/102,780, filed on Oct. 2, 1998.

(51) Int. Cl.$^7$ ............................................... C07C 233/00
(52) U.S. Cl. ........................... 554/52; 554/51; 510/119; 510/130; 510/137; 510/138; 424/70.1; 424/401; 8/405
(58) Field of Search ..................... 554/51, 52; 510/119, 510/130, 137, 138; 424/70.1, 401; 8/405

(56) References Cited

U.S. PATENT DOCUMENTS

| 4,012,398 A | 3/1977 | Conner et al. |
| 4,631,187 A | 12/1986 | Padden et al. |
| 4,734,277 A | 3/1988 | Login |
| 4,978,526 A | 12/1990 | Gesslein et al. |

*Primary Examiner*—Deborah Carr
(74) *Attorney, Agent, or Firm*—Lerner, David, Littenberg, Krumholz & Mentlik, LLP

(57) ABSTRACT

Quaternized monoalkyl compounds derived from fatty acids are described. The quats are produced from fatty acid materials which contain at least about 30% by weight of larger chains containing at least 20 carbons in length. Personal care products produced using these quats are also described.

10 Claims, No Drawings

MONOALKYL QUATS

The present invention claims the benefit of the U.S. Provisional Application No. 60/102,780 filed on Oct. 2, 1998, the disclosure of which is incorporated by reference herein.

FIELD OF THE INVENTION

The present invention relates to novel monoalkyl quaternary fatty ammonium derivatives of natural and synthetic oils, fatty acids and/or triglycerides and to their use in personal care products.

BACKGROUND OF THE INVENTION

U.S. Pat. No. 4,012,398 describes quaternary halides of mink oil amides. These compounds, generally referred to as "quats", are disclosed as being useful emollients having surprisingly good hair conditioning properties. These quats are prepared, for example, by reacting either ethylene chlorohydrin or ethylene bromohydrin in a mixture of water and propylene glycol with an amide obtained by reacting, under anhydrous conditions, mink oil with certain amines using an alkaline catalyst such as sodium hydroxide.

While the mink oil derived quats described in the '398 patent may be suitable for use in certain hair conditioning products, they are unlikely candidates for use in conditioning shampoos. Quats of compounds like mink oil such as those described in the '398 patent while superior in some properties tend to have limited compatibility with anionic surfactants. Thus, while they may be suitable as conditioning agents, their use in shampoo could be problematic. Moreover, even if, sufficiently water soluble and compatible with anionic surfactants, mink oil quats do not provide suitable properties such as sufficient viscosity enhancement to warrant their inclusion in shampoo formulations.

Monoalkyl quats of other fatty acids are also known. For example, U.S. Pat. No. 4,978,526 discloses an amidoamine containing monoalkyl quat of 7 to 24 carbon atoms having a 2, 3 dihydroxypropyl ammonium group. U.S. Pat. No. 4,631,187 describes the use of a monofatty erucyl quat to make hair conditioners. Specifically, the quat described was dimethyl benzyl erucyl ammonium chloride. This compound did not include the use of an amidoamine.

Finally, hydroxyethyl behenamidopropyl dimonium chloride has been sold under the name INCROQUAT BEHENYL HE by Croda, Inc., 7 Century Drive, Parsippany, N.J. 07054.

The difficulty with most, if not all, of these compounds is that, at the activities desirable for commercial sale i.e. 25% to 90%, the resulting materials are solid or semi-solid at room temperature. This requires that both the additive and the shampoo, conditioner or other personal care product to which it will be added be heated during formulation. Heating these products is very expensive. In addition, it could have undesirable effects on the composition by promoting cross reactions between the other constituents, loss of color or clarity, precipitation and the like. In addition, in personal care products containing biological materials such as, for example, proteins, botanical extracts or vitamins, it can either volatize same or inactivate same. Therefore there remains a need for a commercially viable conditioning agent useful in shampoo and conditioners and the like, preferably one which is liquid at room temperature, at commercially desirable activities, and which can nonetheless promote viscosity without sacrifice of anionic surfactant compatibility.

SUMMARY OF THE INVENTION

The present invention relates to the monoalkyl quats of fatty acid materials having at least about 30% of at least a C-20 fatty acid component by weight. If 100% erucic acid is used, then 100% of the fatty acid constituents of the quats is C-22. If HEAR oil is used, then at least 30% of the fatty acids, and therefore at least 30% of the quats, will have a C-20 or higher chain length component. As should be clear, this means that the fatty acid component can be made up of one or more C-20 or greater fatty acids totally at least 30% by weight. In addition, the fatty acids, fatty acid containing oils, triglycerides, waxes and the like useful in accordance with the present invention contain fatty acids having an iodine value of greater than 0. In the case of fatty acid containing oils, this does not mean that all of the constituents must be unsaturated. However, overall, the iodine value must be greater than 0. Preferably, fatty acid constituents will be such that when reacted to form the monoalkyl quats of the present invention, and provided in solvents at activities as discussed herein, they will be liquid at room temperature. Thus, at least 30% of the fatty acid constituents of the resulting quats will generally range from about C-20 to about C-24 in carbon chain length. Finally, the monoalkyl quats of the present invention have superior viscosity properties when compared to quats made from, for example, mink oil, while at the same time, maintaining significant anionic surfactant compatibility allowing them to be easily formulated in, for example, shampoos.

DETAILED DESCRIPTION OF THE PREFERRED EMBODIMENTS

Oils in accordance with the present invention include, without limitation, HEAR oil, as well as cod liver oil, herring oil, menhaden oil, mustard seed oil, pilchard oil, HEAR oil, salmon oil, sardine oil, meadowfoam oil and shark liver oil. The C-20+ components of some of these oils are as follows: Cod liver oil—8.8–14.6% Eicosenoic acid (C20:1), 2.6–9% Eicosapentaenoic acid (C20:5), 4.6–13.3% Docosenoic (Erucic) acid (C22:1), 1–2% Docosapentaenoic acid (C22:5) and 8.6–19% Docosahexaenoic acid (C22:6); Herring oil—1.5–19.2% Eicosenoic acid (C20:1), 4.6–10.2% Eicosapentaenoic acid (C20:5), 2.8–19.9% Docosenoic (Erucic) acid (C22:1), 1–3.7% Docosapentaenoic acid (C22:5) and 3.8–24.1% Docosahexaenoic acid (C22:6); Menhaden oil—0.9–2.7% Eicosenoic acid (C20:1), 0.6–1.2% Eicosatetraenoic acid (C20:4), 10.2–13.5% Eicosapentaenoic acid (C20:5), 0.7–1.7% Docosenoic (Erucic) acid (C22:1), 1.1–2.3% Docosapentaenoic acid (C22:5) and 3.3–14% Docosahexaenoic acid (C22:6); Pilchard (Sardine) oil—3.2% Eicosenoic acid (C20:1), 1.6% Eicosatetraenoic acid (C20:4), 16.9% Eicosapentaenoic acid (C20:5), 3.6% Docosenoic (Erucic) acid (C22:1), 2.5% Docosapentaenoic acid (C22:5) and 12.9% Docosahexaenoic acid (C22:6); HEAR oil—0.8–13.5% Eicosenoic acid (C20:1), 20.1–59.4% Docosenoic (Erucic) acid (C22:1), 0.1–1.4% Tetrcosanoic (C24:0); Mustard Seed oil—7% Eicosenoic acid (C20:1), 44.2% Docosenoic (Erucic) acid (C22:1). Oils rich in Tetracosaenoic (Nervonic) acid (C24:1) such as genetically altered HEAR oil also work well. Of course, variations in content can occur. See generally 1 "Bailey's Industrial Oil and Fat Products" (Daniel Swern, John Wiley & Sons, 4th Ed. 1979) pg. 416, 417, 447, 449, 450 and 452, all of which are attached and hereby incorporated by reference.

Each of the foregoing oils has a distribution of fatty acids (usually in the form of trigylcerides) which includes at least 30% of a C-20 or greater component. Mink oil, in contrast, is predominantly oleic acid (C18:1), palmitoleic acid (C16:1), linoleic acid (C18:2), palmitic acid (C16:0), and steric acid (C18:0). Only trace amounts of fatty acids components having a chain length of twenty carbons or longer are present.

Of course, it is possible in accordance with the present invention to use pure fatty acids and/or artificially created mixtures including, without limitation gadoleic (C20:1), erucic (C22:1), arachadonic (C20:4) and culpodonic (C22:5). Mixtures of fatty acids are also possible which include fatty acid constituents of lower carbon chain lengths. Fatty acids may be provided from fatty acid containing oils, triglycerides and as fatty acids, esters or salts. Indeed, fatty acid materials useful for production of monoalkyl quats in accordance with the present invention can come from natural or synthetic sources and include pure fatty acids, fatty acid mixtures, triglycerides, oils, and waxes such as, for example, jojoba oil (fatty acids and fatty alcohols).

The fatty acids should also be limited in terms of the degree of saturation. Preferably the majority of the fatty acid materials will be unsaturated. One way of measuring the degree of saturation of fatty acids is the well known iodine value used in the trade. Odor and color problems can develop as the iodine value of a fatty acid or oil containing fatty acid increases due to the products being more prone to oxidation. The odor and very dark colors obtained render the quats unacceptable for use as cosmetic ingredients. It may also render the compounds difficult to work with and compatibilize. This is particularly true when it is desired to include these ingredients in, for example, conditioning shampoos. Therefore, esters, triglycerides, acids or any combination thereof and/or the individual fatty acids should preferably have an iodine value of 200 or less, more preferably 150 or less, most preferably 100 or less. However, in the case of the monoalkyl quats of the present invention, the iodine value should be greater than 0. Thus, fatty acids and/or oils composed exclusively of completely saturated constituents are excluded. Such components are, in general, incapable of being formulated as liquids at room temperature at any meaningful activity level.

Quats produced in accordance with the present invention would generally be unusable for cosmetic purposes in pure form. They exist as salts, with counter ions being present for the cationic quaternary group. These salts can include halogen ions, sulfates, phosphates and the like. Typically, therefore, quats in accordance with the present invention are manufactured in a cosmetically acceptable solvent. The cationic activity of a quat is used to measure the content of the quats disbursed or dissolved in the solvent in a percent by weight basis. Thus, a quat that has 50% cationic activity is provided in a 50% weight ratio to the solvent. Monoalkyl quats made from behenic acid, for example, are solid at room temperature when sold at commercially viable cationic activities. At about 30% cationic activity, formulations of behenic acid based quats in hexylene glycol are still a paste requiring heating for use. In addition, behenic based quats are not compatible with various solvents such as, for example, propylene glycol. This solvent incompatibility further limits the usefulness of these materials.

In accordance with the present invention, however, quats are made from fatty acids which have an iodine value of greater than 0 and a content of C-20 fatty acids of greater than 30% by weight. That means that the formulations include some level of unsaturation. Most preferably, the substantial components of the fatty acids used have a chain length of between about C-20 and about C-24, although some higher and/or lower chain lengths are also useful as exemplified by HEAR oil.

Most preferably, the resulting quats, at commercially feasible activities, are liquid at room temperature and will not require heating prior to formulation in conditioners or shampoos. Most preferably the quats of the present invention are liquid at room temperature (approximately 25° C.) at cationic activities as high as 75%, and more preferably 65% or below. This means that neither the quats in solvent nor the base i.e. shampoo, conditioner, etc. needs to be heated to facilitate mixing. Of course, either or both can be heated if desired. Quats in accordance with the present invention made from HEAR oil as previously described, for example, are liquid at about 60% cationic activity.

Quats in accordance with the present invention can be made using the techniques generally described in the aforementioned '398 patent, the text of which is hereby incorporated by reference. The novel products of this invention may be prepared as follows. An oil, a triglyceride, a free fatty acid or mixtures thereof is reacted with either gamma dimethylamino (DMAPA) or gamma diethylaminopropylamine (DEAPA) at between about 140°–160° C. using an alkaline catalyst and a nitrogen atmosphere which inhibits oxidation of the unsaturated fatty acids. Alkaline catalysts such as sodium hydroxide, potassium hydroxide and sodium methylate or ethylate work equally well.

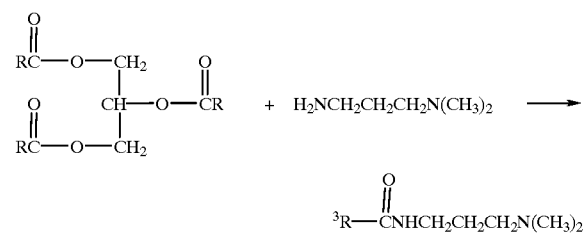

The resulting amidoamine is quaternized with either ethylene chlorohydrin or ethylene bromohydrin at about 105°–115° C. in a solvent mixture of water and propylene glycol. This solvent mixture is used to control the reaction temperature and thus avoid decomposition of the quaternary as it is formed. The fatty amidoamine can then be quaternized as described above or can be neutralized with an acid such as, for example, hydrochloric acid (HCl) and then reacted with ethylene oxide to produce the desired quat.

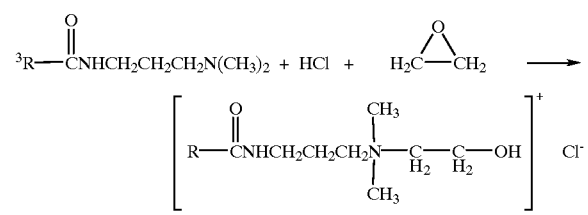

Instead of ethylene oxide, other substituted alkoxy groups may be used such as:

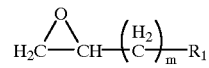

where m=1–6 carbons and $R_1$ is H, $CH_3$ or

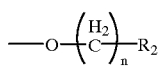

where n=0–6 carbons and $R_2$ is H, $CH_3$ or OH; or $R_1$ is

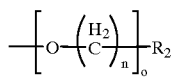

where n is as previously defined and where o=1 to 40 and $R_2$ is H, $CH_3$ or OH.

The methods disclosed generally in Login, U.S. Pat. No. 4,734,277, may also be used to form monoalkyl quats. The Login patent is hereby incorporated by reference.

Quats in accordance with the present invention are produced from amine constituents which can form an amidoamine. Such compounds include a dialkyl amino-alkyl amines such DMAPA, DEAPA and the like. The alkyl group between the nitrogens, and indeed the three other positions on the quaternary nitrogen, can be substituted as is known in the art with, for example, hydroxy groups, longer chain alkyl groups (1–6 carbons), alkyoxy groups, polyalkoxy groups, substituted alkoxy groups and the like. Generally electro negative groups are preferred for anionic surfactant compatibility. Anionic surfactant compatibility can be measured by a clear solution without precipitation or turbidity once the quat is mixed with the surfactant.

Solvents useful in accordance with the present invention include those known in the industry for use in dissolving quats. These include ethylene glycol, propylene glycol, normal alcohol such as ethanol, isopropanol, hexylene glycol, dipropylene glycol, butylene glycol and the like.

A HEAR oil derived quat which can be produced as described in patent 4,012,398 was compared with the mink oil analogue in a shampoo base consisting of the following:

|  | % W/W |
| --- | --- |
| Ammonium lauryl sulfate | 31.250 |
| Cocamide DEA | 3.125 |
| Germaden II | 1.000 |
| Water | 64.620 |

This base had a viscosity of 20 cps at 25° C. Two systems were put together consisting of 95% of the above base and 2.5% active mink quat or HEAR quat. The mink quat system had a viscosity of 1650 cps. The hear quat system had a viscosity of 6850 cps. Both viscosities were determined at 25° C. The hear oil derived quat has a clear advantage building viscosity than the mink oil.

Generally, the quats in accordance with the present invention are provided in an amount of between about 25 and 90% by weight relative to the amount of solvent. More preferably between about 25 and 80% and even more preferably between 25 and 65% by weight. In addition, fatty acids or fatty alcohols can also be used resulting in a flakable material.

The formulations in accordance with the present invention are often referred to, when mixed with their solvent, as containing a certain amount of cationic activity. Therefore, a formulation including a 25% cationic activity consists of, amongst other things, 25 weight percent of a cationic quat in 75 weight percent of a solvent. Generally, the quats of the present invention are formulated in shampoos in an amount of between about 1 and about 10 percent based on the amount of cationic activity. Therefore, in formulating a shampoo with, for example, 1% active or 1% cationic activity, 2% of a 50/50 quat/solvent formulation by weight of the shampoo would be necessary for formulation. More preferably, the amount of activity ranges from between about 1% and about 5% and more preferably between about 0.5% and about 3%. On an actives basis, generally the same amounts may be used in conditioners.

What is claimed is:

1. A monoalkyl quat material comprising a quaternized monoalkyl amidoamine wherein said monoalkyl group has an iodine value of greater than 0 and includes at least about 30% of at least a C-20 fatty acid component by weight, said quaternized monoalkyl amidoamine being dissolved or dispersed in a solvent at a cationic activity of between about 25% and about 90%.

2. The monoalkyl quat material of claim 1 wherein said monoalkyl group has an iodine value of between greater than 0 and about 200.

3. The monoalkyl quat material of claim 2 wherein said monoalkyl quats and solvent are, when combined, in a liquid form at 25° C.

4. The monoalkyl quat material of claims 1, 2 or 3 wherein said monoalkyl group is derived from the fatty acids contained in triglycerides, waxes or an oil selected from the group consisting of HEAR oil, cod liver oil, herring oil, menhaden oil, mustard seed oil, pilchard oil, hear oil, salmon oil, sardine oil, meadowfoam oil and shark liver oil.

5. The monoalkyl quat material of claims 1, 2 or 3 wherein said monoalkyl group is derived from the fatty acids selected from the group consisting of Eicosenoic acid, Eicosapentaenoic acid, Erucic acid, 1–2% Docosapentaenoic acid, Docosahexaenoic acid, Eicosatetraenoic acid, Tetrcosanoic acid, arachidic acid, behemic acid, gadoleic acid, arachadonic acid and culpodonic acid.

6. The monoalkyl quat material of claims 1, 2 or 3 further comprising a shampoo base, conditioner base, facial soap base, hair color base or body wash base said monoalkyl quats being provided in an amount of between about 0.1 and about 10% cationic activity by weight.

7. The monoalkyl quat material of claim 1 wherein said amidoamine includes an alkoxy, substituted alkoxy, alkyl, hydroxy or polyalkoxy group.

8. A personal care product comprising: a shampoo base, conditioner base, facial soap base, hair color base, body wash base or liquid soap base and between about 0.1 to about 10% by activity of a monoalkyl quat material comprising a quaternized monoalkyl amidoamine wherein said monoalkyl group has an iodine value of greater than 0 and includes at least about 30% of at least a C-20 fatty acid component by weight, said quaternized monoalkyl amidoamine being dissolved or dispersed in a solvent.

9. The personal care product of claim 8 wherein said monoalkyl group is derived from the fatty acids contained in triglycerides, waxes or an oil selected from the group consisting of HEAR oil, cod liver oil, herring oil, menhaden oil, mustard seed oil, pilchard oil, hear oil, salmon oil, sardine oil, meadowfoam oil and shark liver oil.

10. The personal care product of claim 8 wherein said monoalkyl group is derived from the fatty acids selected from the group consisting of Eicosenoic acid, Eicosapentaenoic acid, Erucic acid, 1–2% Docosapentaenoic acid, Docosahexaenoic acid, Eicosatetraenoic acid, Tetrcosanoic acid, arachidic acid, behemic acid, gadoleic acid, arachadonic acid and culpodonic acid.

* * * * *

UNITED STATES PATENT AND TRADEMARK OFFICE
CERTIFICATE OF CORRECTION

PATENT NO. : 6,399,799 B1
DATED : June 4, 2002
INVENTOR(S) : Abel Pereira

It is certified that error appears in the above-identified patent and that said Letters Patent is hereby corrected as shown below:

<u>Column 6,</u>
Line 1, "1" should read -- .1 --.
Line 7, "1%" should read -- .1% --.

Signed and Sealed this

Thirty-first Day of December, 2002

JAMES E. ROGAN
*Director of the United States Patent and Trademark Office*